US007074198B2

(12) United States Patent
Krullaards

(10) Patent No.: US 7,074,198 B2
(45) Date of Patent: Jul. 11, 2006

(54) METHODS FOR TREATMENT AND PREVENTION OF DISORDERS RESULTING FROM HYPERTENSION OF NECK AND SHOULDER MUSCLES

(75) Inventor: Robert Leonard Krullaards, Leidschendam (NL)

(73) Assignees: Tensor, B.V., AT Zoetermeer (NL); Smartsense, B.V., HG Breda (NL)

( * ) Notice: Subject to any disclaimer, the term of this patent is extended or adjusted under 35 U.S.C. 154(b) by 615 days.

(21) Appl. No.: 10/268,614

(22) Filed: Oct. 9, 2002

(65) Prior Publication Data

US 2003/0149379 A1 Aug. 7, 2003

Related U.S. Application Data

(63) Continuation-in-part of application No. 10/168,725, filed as application No. PCT/NL00/00957 on Dec. 22, 2000, now abandoned.

(51) Int. Cl.
*A61B 5/103* (2006.01)
*A61B 5/117* (2006.01)

(52) U.S. Cl. ...................... 600/587; 600/300; 600/301; 600/595; 73/379.01; 73/379.02

(58) Field of Classification Search ................ 600/301, 600/587, 595, 300; 73/379.01, 379.02
See application file for complete search history.

(56) References Cited

U.S. PATENT DOCUMENTS 4,467,815 A * 8/1984 O'Brien et al. ............. 600/553
4,807,642 A 2/1989 Brown
5,174,154 A * 12/1992 Edwards .................. 73/379.02
5,184,628 A * 2/1993 Shah et al. ................. 600/587
5,220,308 A 6/1993 Batzdorff et al.
5,447,167 A 9/1995 Fleischaker
5,467,656 A 11/1995 Teare et al.
5,513,651 A * 5/1996 Cusimano et al. .......... 600/595
5,579,238 A * 11/1996 Krugman ..................... 702/41
5,642,096 A 6/1997 Leyerer et al.
5,681,993 A * 10/1997 Heitman .................. 73/379.02
5,745,376 A * 4/1998 Barker et al. ................. 702/41
5,904,639 A * 5/1999 Smyser et al. ................ 482/91
5,964,719 A 10/1999 Costello et al.
6,264,621 B1 * 7/2001 Paske ......................... 600/587
6,267,733 B1 * 7/2001 Peterson et al. ............ 600/587
6,375,622 B1 * 4/2002 Kao et al. ................... 600/485
6,425,764 B1 * 7/2002 Lamson ...................... 434/236
6,489,947 B1 12/2002 Hesley et al.
6,579,209 B1 * 6/2003 Valette et al. .................. 482/8
6,678,549 B1 * 1/2004 Cusimano et al. .......... 600/546
6,855,112 B1 * 2/2005 Kao et al. ................... 600/300

FOREIGN PATENT DOCUMENTS

NL 1006708 8/1997
WO WO 90/14792 A1 12/1990
WO WO 01/45561 A1 6/2001

* cited by examiner

*Primary Examiner*—Max F. Hindenburg
*Assistant Examiner*—Rene Towa
(74) *Attorney, Agent, or Firm*—Townsend and Townsend and Crew LLP

(57) ABSTRACT

Methods for treatment and prevention of disorders resulting from hypertension of neck and shoulder muscles, in particular hypertension of the scalenius muscles, comprise administering a training regime to a subject suffering from the disorders, whereby the training regime comprises manipulating an object while maintaining a pinch-grip force exerted by the fingers on the object below a given threshold value. The object preferably has a pressure sensor that generates a signal when the pinch-grip force exceeds the threshold value. The object may be a writing instrument whereby the training may comprise writing exercises.

23 Claims, 19 Drawing Sheets

48 40 49 5 47 44 45 46 41 42 43

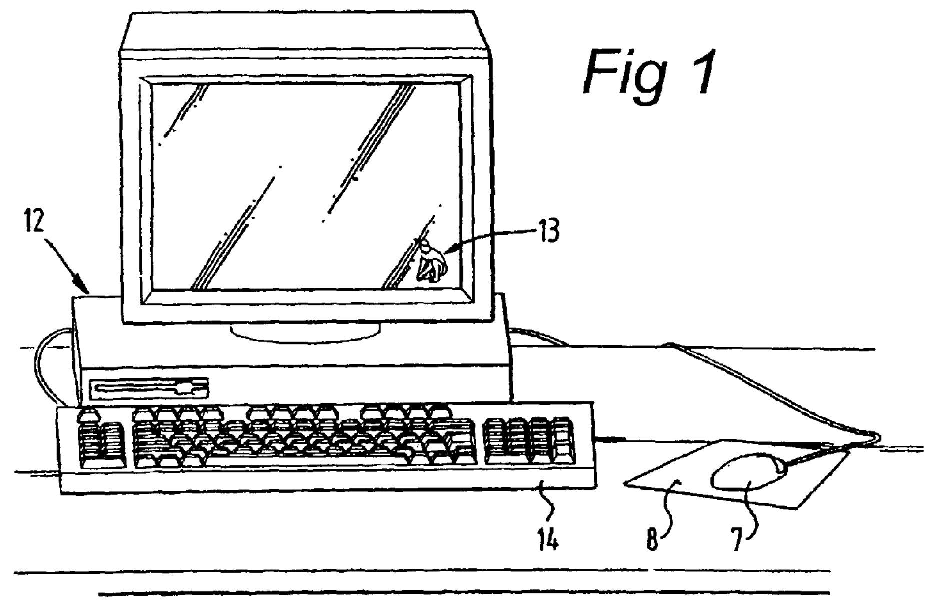
Fig 1
12
13
14
8
7
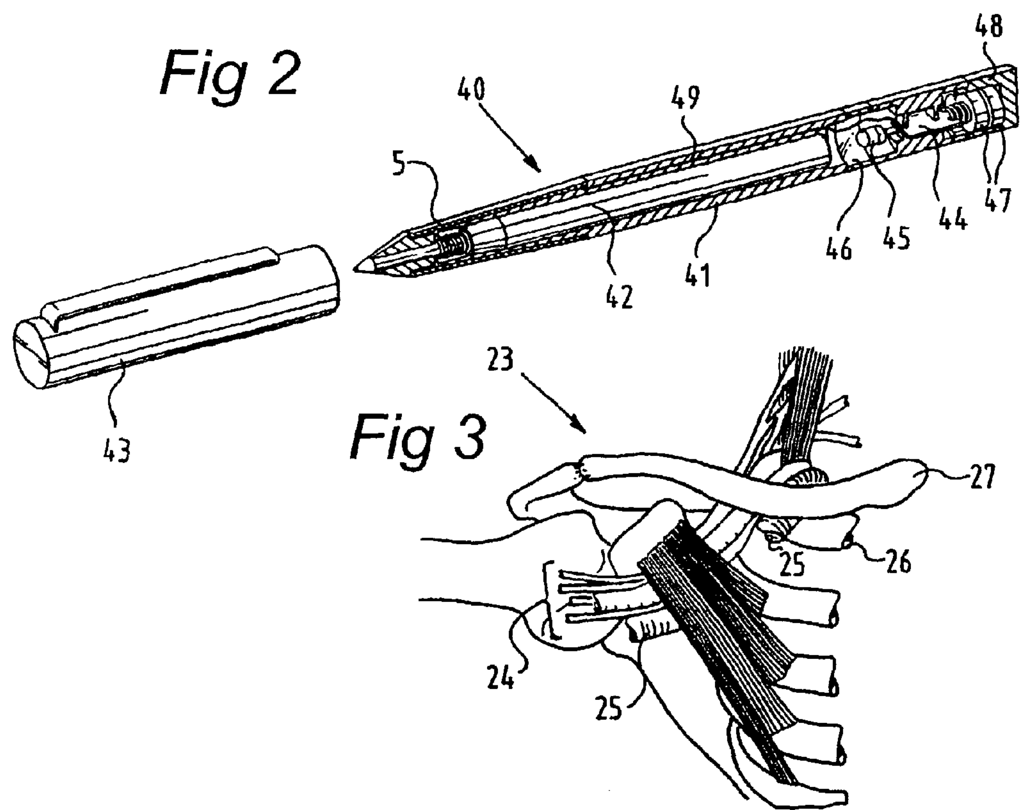
Fig 2
48
40
49
5
47
44
46
45
41
42
43
23
Fig 3
27
25
26
24
25

15

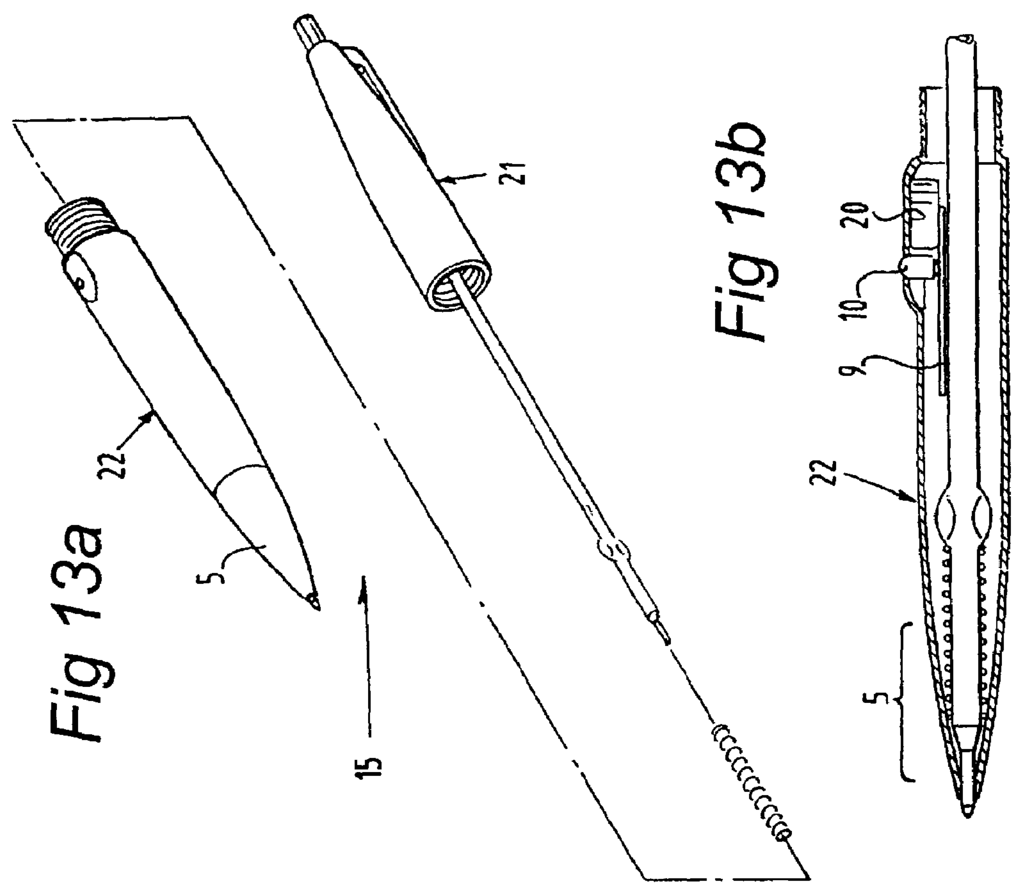
Fig 13a
22
5
15
21
Fig 13b
20
10
9
22
5
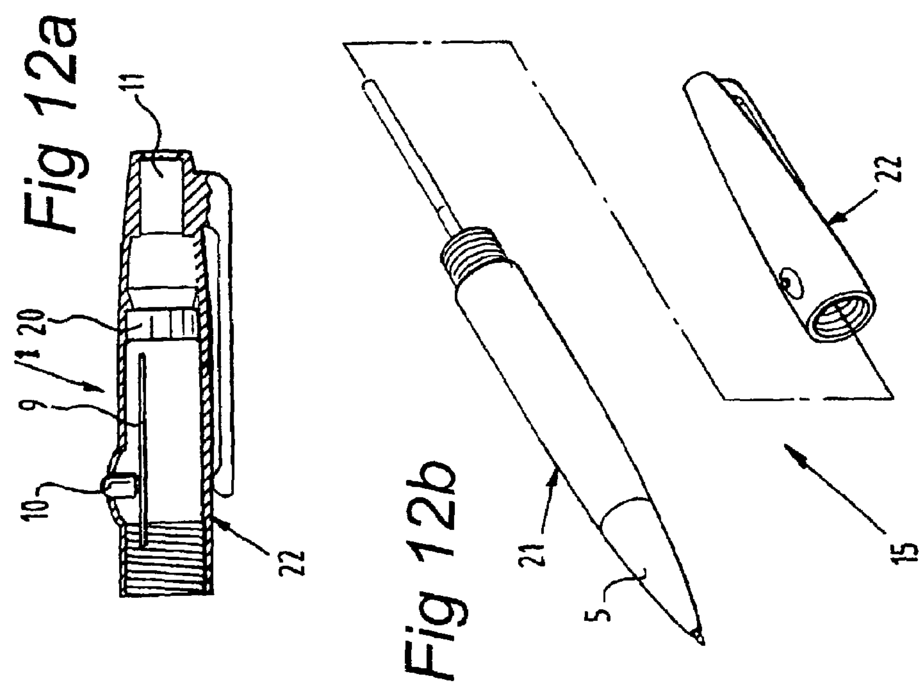
Fig 12a
11
20
9
1
10
22
Fig 12b
21
5
22
15

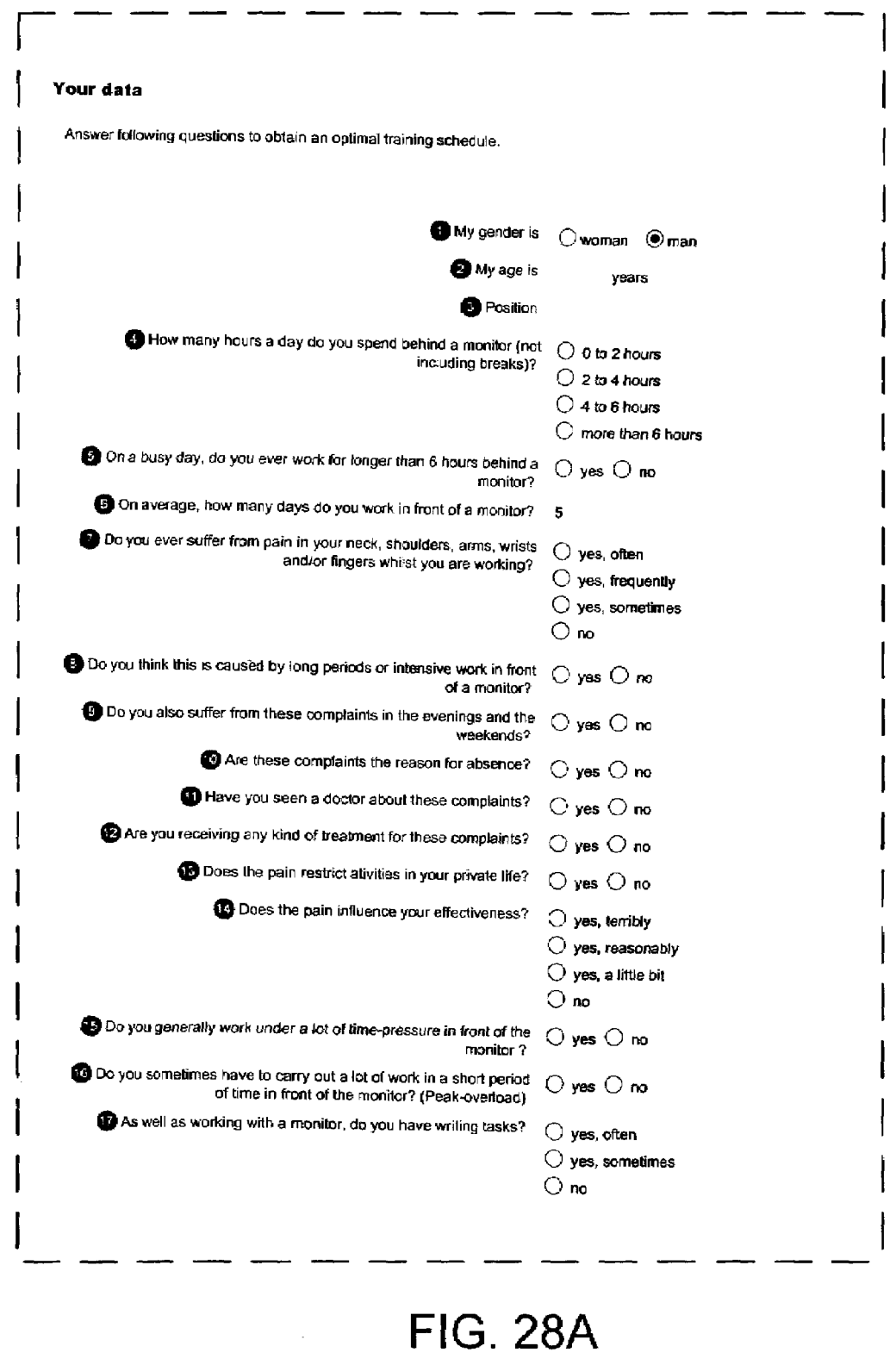

Your data

Answer following questions to obtain an optimal training schedule.

1 My gender is ◯ woman ◉ man

2 My age is years

3 Position

4 How many hours a day do you spend behind a monitor (not including breaks)? ◯ 0 to 2 hours ◯ 2 to 4 hours ◯ 4 to 6 hours ◯ more than 6 hours 5 On a busy day, do you ever work for longer than 6 hours behind a monitor? ◯ yes ◯ no 6 On average, how many days do you work in front of a monitor? 5

7 Do you ever suffer from pain in your neck, shoulders, arms, wrists and/or fingers whilst you are working? ◯ yes, often ◯ yes, frequently ◯ yes, sometimes ◯ no 8 Do you think this is caused by long periods or intensive work in front of a monitor? ◯ yes ◯ no 9 Do you also suffer from these complaints in the evenings and the weekends? ◯ yes ◯ no 10 Are these complaints the reason for absence? ◯ yes ◯ no 11 Have you seen a doctor about these complaints? ◯ yes ◯ no 12 Are you receiving any kind of treatment for these complaints? ◯ yes ◯ no 13 Does the pain restrict ativities in your private life? ◯ yes ◯ no 14 Does the pain influence your effectiveness? ◯ yes, terribly ◯ yes, reasonably ◯ yes, a little bit ◯ no 15 Do you generally work under a lot of time-pressure in front of the monitor ? ◯ yes ◯ no 16 Do you sometimes have to carry out a lot of work in a short period of time in front of the monitor? (Peak-overload) ◯ yes ◯ no 17 As well as working with a monitor, do you have writing tasks? ◯ yes, often ◯ yes, sometimes ◯ no

FIG. 28A

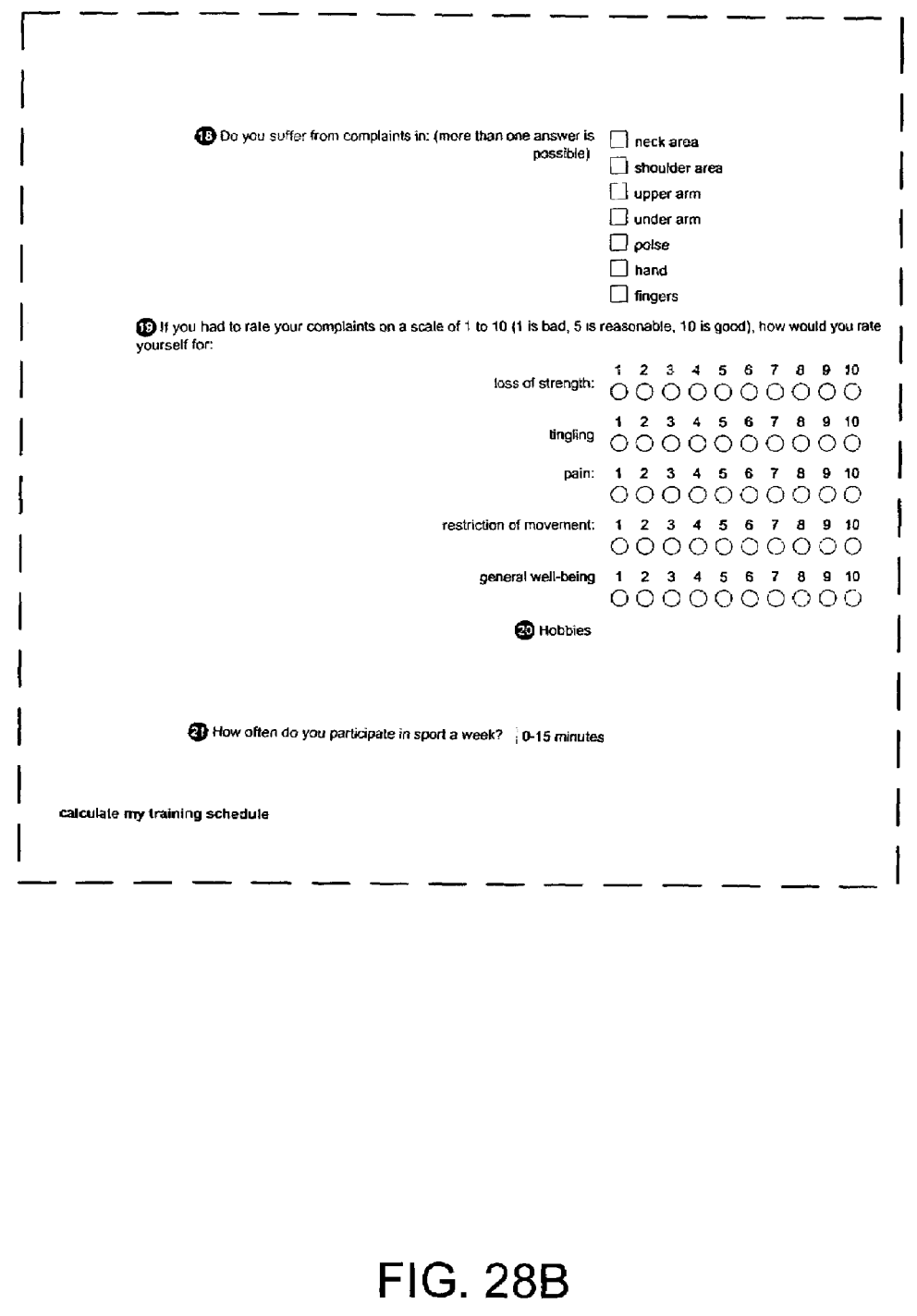

18 Do you suffer from complaints in: (more than one answer is possible)

- ☐ neck area
- ☐ shoulder area
- ☐ upper arm
- ☐ under arm
- ☐ polse
- ☐ hand
- ☐ fingers 19 If you had to rate your complaints on a scale of 1 to 10 (1 is bad, 5 is reasonable, 10 is good), how would you rate yourself for:

| | 1 | 2 | 3 | 4 | 5 | 6 | 7 | 8 | 9 | 10 |
|---|---|---|---|---|---|---|---|---|---|---|
| loss of strength: | ○ | ○ | ○ | ○ | ○ | ○ | ○ | ○ | ○ | ○ |
| tingling | ○ | ○ | ○ | ○ | ○ | ○ | ○ | ○ | ○ | ○ |
| pain: | ○ | ○ | ○ | ○ | ○ | ○ | ○ | ○ | ○ | ○ |
| restriction of movement: | ○ | ○ | ○ | ○ | ○ | ○ | ○ | ○ | ○ | ○ |
| general well-being | ○ | ○ | ○ | ○ | ○ | ○ | ○ | ○ | ○ | ○ |

20 Hobbies

21 How often do you participate in sport a week? 0-15 minutes calculate my training schedule

FIG. 28B

A Draw a second circle with a dot in the middle or print the circle form.
Put the pen in circle 1 on the dot and then in circle 2 on the dot. Make sure that no signal is given.
Repeat this 10 times and count the number of times that the pen gives a signal.

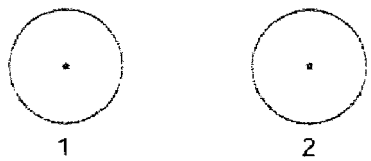

B See exercise a.
Join the circles with a straight line without leaving the paper. Then continue going back and forth from 1 to 2 ten times.

C Start with the pen on the line at point 1, going from 1 to 2 to 3 and back to 1. Increase the speed.
Complete this 10 times after another keeping the pen on the paper.

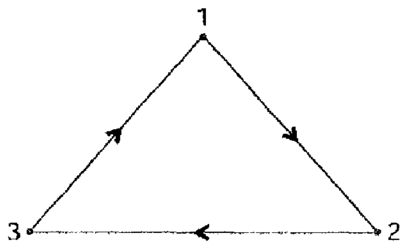

Watch out

Count the total number of times that the pen gave a signal.

FIG. 31

Distance between 1 - 2 - 3 - 4 is 10 centimeters. In the above figure the distance is not 10 centimeters. Copy the figure of print it by clicking on "Print exercise".

Join the circles with the following pattern:

A 1 > 2
2 > 4
4 > 3
3 > 4

B 1 > 5
5 > 2
2 > 4
4 > 5
5 > 3
3 > 1

Watch out

Repeat A and B ten times without leaving the paper.
Count the total number of times that the pen gave a signal.

Print the figure by clicking on "Print exercise"
Join the dots together in a continuous line so that the figure becomes visible, keeping contact with the paper.

norsi

Watch out

Keep contact with the paper.
Count the total number of times that the pen gave a signal.

FIG. 33

A Write the N -line. Write from left to right and repeat twice.

nnnnnnnnnnnnnnnnnnnnnnn

B Write the e -line. Write the line from left to right and repeat twice.

eeeeeeeeeeeeeeeeeeeeeeeeeeee

C Write the o -line. Write the line twice from left to right.

oooooooooooooooooooooo

Watch out

Keep contact with the paper.
Count the total number of times that the pen gave a signal.

FIG. 34

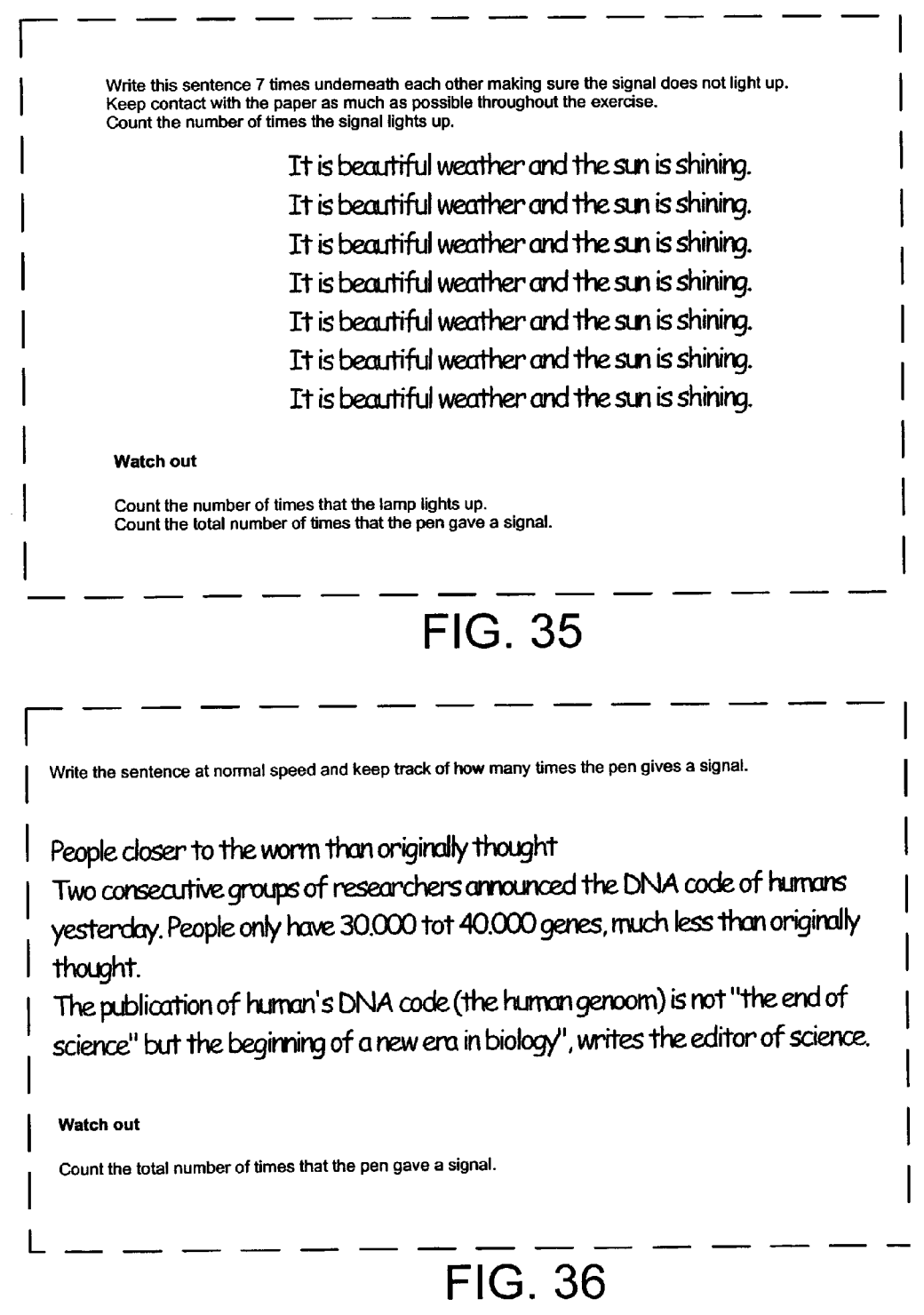

Write this sentence 7 times underneath each other making sure the signal does not light up.
Keep contact with the paper as much as possible throughout the exercise.
Count the number of times the signal lights up.

It is beautiful weather and the sun is shining.
It is beautiful weather and the sun is shining.
It is beautiful weather and the sun is shining.
It is beautiful weather and the sun is shining.
It is beautiful weather and the sun is shining.
It is beautiful weather and the sun is shining.
It is beautiful weather and the sun is shining.

Watch out

Count the number of times that the lamp lights up.
Count the total number of times that the pen gave a signal.

FIG. 35

Write the sentence at normal speed and keep track of how many times the pen gives a signal.

People closer to the worm than originally thought
Two consecutive groups of researchers announced the DNA code of humans yesterday. People only have 30.000 tot 40.000 genes, much less than originally thought.
The publication of human's DNA code (the human genoom) is not "the end of science" but the beginning of a new era in biology", writes the editor of science.

Watch out

Count the total number of times that the pen gave a signal.

FIG. 36

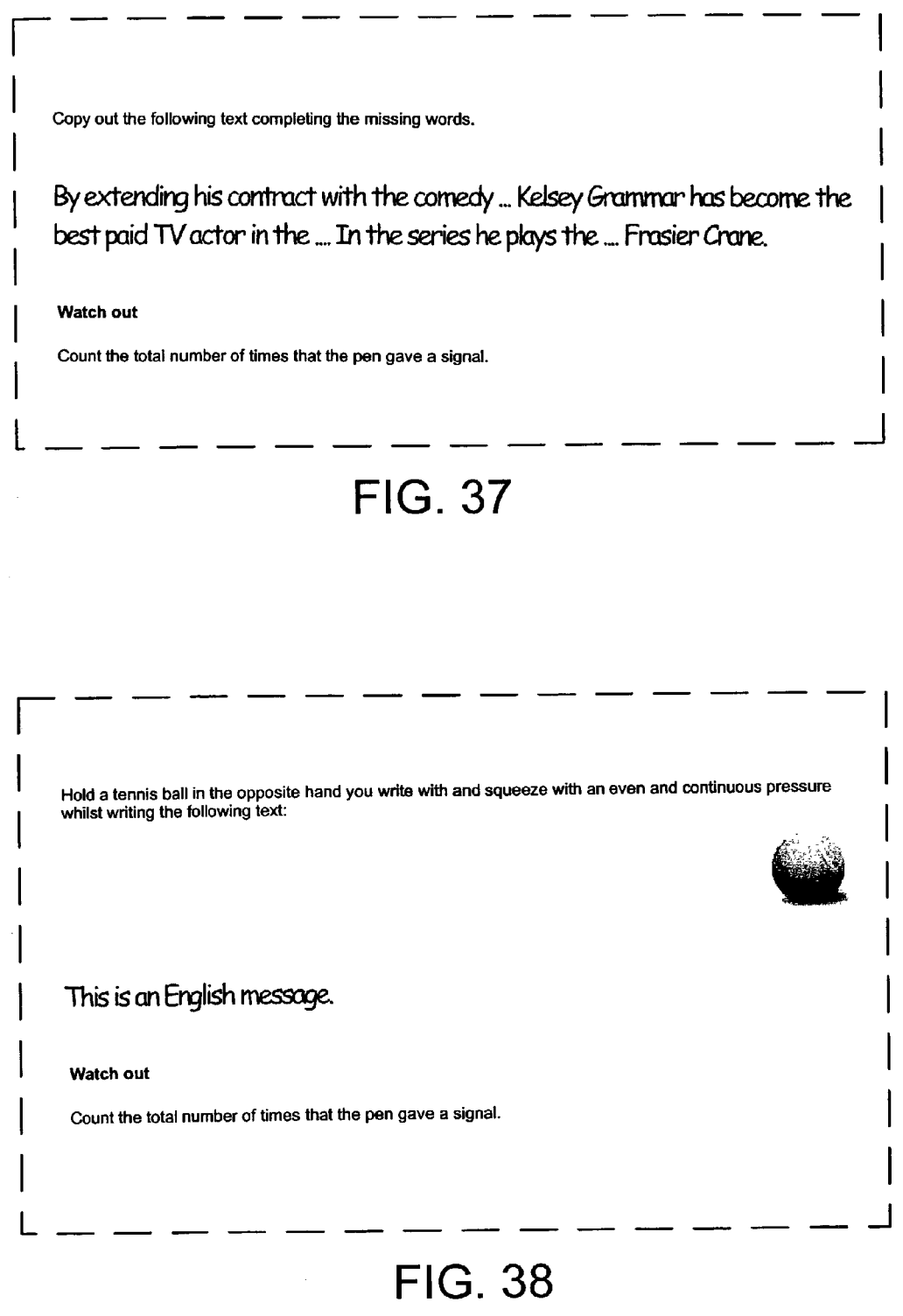

Copy out the following text completing the missing words.

By extending his contract with the comedy ... Kelsey Grammar has become the best paid TV actor in the .... In the series he plays the .... Frasier Crane.

Watch out

Count the total number of times that the pen gave a signal.

FIG. 37

Hold a tennis ball in the opposite hand you write with and squeeze with an even and continuous pressure whilst writing the following text:

This is an English message.

Watch out

Count the total number of times that the pen gave a signal.

FIG. 38

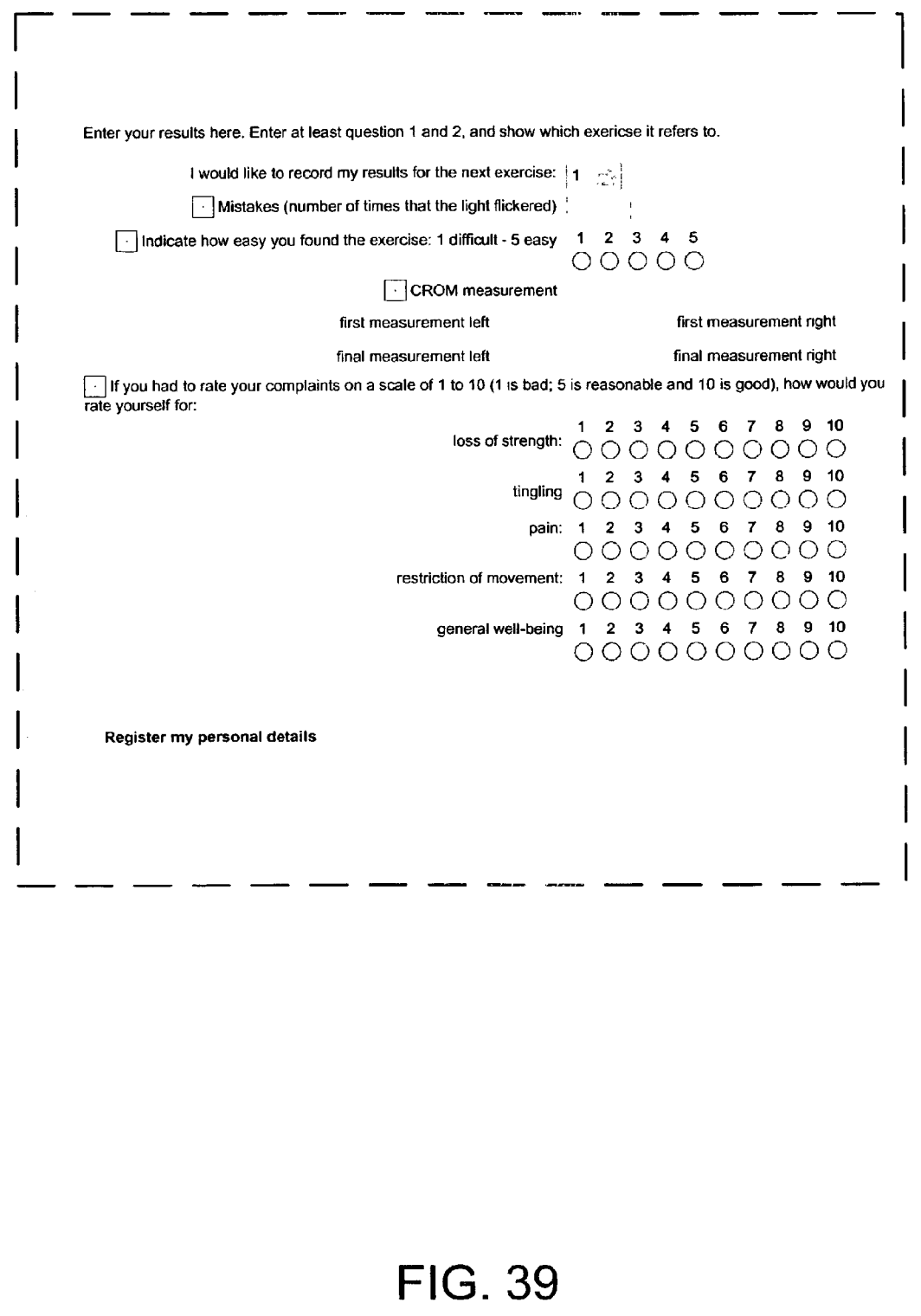

Enter your results here. Enter at least question 1 and 2, and show which exericse it refers to.

I would like to record my results for the next exercise: 1

☐ Mistakes (number of times that the light flickered)

☐ Indicate how easy you found the exercise: 1 difficult - 5 easy 1 2 3 4 5

☐ CROM measurement first measurement left first measurement right final measurement left final measurement right ☐ If you had to rate your complaints on a scale of 1 to 10 (1 is bad; 5 is reasonable and 10 is good), how would you rate yourself for:

loss of strength: 1 2 3 4 5 6 7 8 9 10 tingling 1 2 3 4 5 6 7 8 9 10 pain: 1 2 3 4 5 6 7 8 9 10 restriction of movement: 1 2 3 4 5 6 7 8 9 10 general well-being 1 2 3 4 5 6 7 8 9 10

Register my personal details

FIG. 39

METHODS FOR TREATMENT AND PREVENTION OF DISORDERS RESULTING FROM HYPERTENSION OF NECK AND SHOULDER MUSCLES

CROSS-REFERENCES TO RELATED APPLICATIONS

This application is a continuation-in-part of application Ser. No. 10/168,725, now abandoned, filed on Oct. 24, 2002, corresponding to the National Phase of PCT/NL00/00957, filed Dec. 22, 2000, which claimed the benefit of the Netherlands Patent No. NE 1013921, filed on Dec. 22, 1999, the full disclosures of which are incorporated herein by reference.

BACKGROUND OF THE INVENTION

1. Field of the Invention

The present invention relates to methods for treatment and prevention of disorders resulting from hypertension of neck and shoulder muscles, in particular hypertension of the scalenius muscles. The method comprises administering a training regime to a subject suffering from the disorders, whereby the training regime comprises manipulating an object while maintaining the pinch-grip force exerted by the fingers on the object below a given threshold value. The object preferably has a pressure sensor that generates a signal when the pinch-grip force exceeds the threshold value.

In recent times many problems have arisen in relation to the results of tensions prevailing in human muscles. "RSI" in particular has received much media attention in recent times. The problem of "tennis elbow" has however been known for much longer.

These problems are caused by maintaining directly or indirectly too high a muscle tension in the arm, neck or shoulders for too long, which causes too high a tension in the neck-shoulder area, whereby neurological and vascular symptoms occur.

These problems can also be brought about by other causes, such as an incorrect posture, stress, writing rapidly and without a break, an inappropriate arrangement of the working surface or the desk or other causes forcing the neck or shoulders into too high a position, or holding them in such a position or by trauma, such e.g. a whiplash.

It is an object of the present invention to provide for methods for the treatment and prevention of such disorders associated with hypertension in the neck-shoulder area, as well as to provide for devices that may be applied in such methods.

2. Description of the Background Art

U.S. Pat. No. 5,447,167, describes a pen having an integral sensor for signaling the application of excessive force. U.S. Pat. Nos. 5,579,238 and 5,220,308 and published PCT application WO 90/14792 describe biofeedback apparatus. Netherlands Patent No. 1006708 describes various hand-held devices with integral sensors.

BRIEF SUMMARY OF THE INVENTION

The scalenius muscles (FIG. 26) are a group of muscles that run from the first rib to several vertebras in the neck. The scalenius muscles are postural muscles whose main function is to stabilize the neck spinal column. Intense activity, emotion, strain, stress and/or trauma can cause hypertension of the scalenius muscles (51 and 52). Hypertension of the scalenius muscles causes too much pressure on the intervertebral discs in the neck and raises the position of the first rib or costa I(26), which causes a narrowing of the costoclavicular gate (56). The costoclavicular gate is the space that is confined by the first rib and the collarbone or clavicula (27). The vasculature and nerves that serve the arms run through this costoclavicular gate. Narrowing of the costoclavicular gate causes constriction (impingement) of this vasculature and nerves, in particular the artery subclavia (53), the vena subclavia (54) and the plexus brachialis (55). Constriction of this vasculature and nerves causes a number of complaints in the arms and shoulders. Moreover, the increased pressure on the intravertebral discs may cause further problems in the neck area, such as bulging of the intravertebral discs. Bulging can cause irritation of the nerve roots that protrude from the neck spinal column and can cause irritation and inflammation of the facet joints, which may result in pain and (arthrogenic) loss of mobility.

As a consequence, a wide variety of disorders results from, or is associated with hypertension of the scalenius muscles. Such disorders include repetitive strain injury, acute and chronic post-whiplash syndromes, arthrose and pre-arthrose, discopathy, i.e. pressure on the intervertebral discs in the neck, including narrowing of the discs coinciding with pressure on the nerve roots and associated motor control deficiencies and sensory disorders, reflex dystrophy in the upper extremities and other vegetative disorders (such e.g. dizziness and tinnitis) resulting from hypertension in the neck area, tendinitidis, venous obstruction or reduced venous blood flow, coordination disorders during writing, writingcramp in children, frozen shoulders, headaches, and carpal tunnel syndromes resulting from venous obstruction.

The present inventor has now surprisingly discovered that exercises in which, an object that is held by pinch-grip action of a subject's fingers is manipulated while maintaining the pinch-grip force below a given threshold value, cause relaxation of the scalenius muscles. Interestingly, performing the exercise with one hand causes relaxation of the scalenius muscles on both sides of the body. Thereby these exercises provide a means to treat and prevent disorders that are associated with hypertension of the scalenius muscles.

In a first aspect the present invention therefore relates to a method for treatment and prevention of a disorder associated with or resulting from hypertension of the scalenius muscles in a human subject, the method comprising administering to the subject a training regime comprising an exercise involving the manipulation of an object held by pinch-grip force of the subject's fingers, whereby the object comprises a sensor to monitor the pinch-grip force exerted by the subject's fingers on the object, whereby the sensor generates a first signal when the pinch-grip force exceeds a first threshold value, and whereby the exercise comprises manipulating the object while maintaining the pinch-grip force below the first threshold value. Preferably, the first threshold value is 100, 125, 150, 175, 200 or 250 grams, of which a value in the range of 150–175 grams is most preferred. Children tend to exert more force on the writing instrument compared to adults. The threshold value may therefore be set to a higher value for children, e.g. 180–200 grams.

Preferably in the method of the invention, the time is measured from the moment the first threshold value is exceeded, and a second signal is generated when the measured time exceeds a second threshold value. The second threshold value for the measured time preferably is at least 1.5, 2.0, 2.5, 3.0 or 4.0 seconds.

In a alternative embodiment only the second signal is generated, i.e. only a signal is generated when the pinch-grip force exceeds the first threshold value for a period of time which exceeds the second threshold value for the measured time.

In a further preferred embodiment, a third signal is generated when the measured time exceeds a third threshold value, which is later than the second threshold value for the measured time. The third threshold value for the measured time preferably is 6, 8, 10, 12, or 16 seconds.

In the method of the invention, the first and second, and optional third, signals may be fed to a collective signaling device. Such a collective signaling device is preferably capable of generating different signals, such that the first and second, and optional third signal may be distinguished from each other.

Preferably in the method according to the invention, the exercise is continued until the tension of the scalenius muscles is reduced, more preferably until the hypertension of the scalenius muscles is released. The method may also be used as a sensomotoric training aimed at relaxation of the tension of the scalenius muscles.

The reduction of the tension or the release of hypertension in the scalenius muscles may be determined by measuring an increase in blood flow velocity in the artery radialis or in the artery subclavia. The increase in blood flow velocity is a direct measure for the increase in diameter of the artery radialis or the artery subclavia, resulting from a widening of the costoclavicular gate. The increase in blood flow velocity in the artery radialis or subclavia may be measured by means known to the skilled person per se. Preferably non-invasive methods are used for determining the blood flow velocity including e.g. ultrasound or optical, e.g. laser, Doppler velocimetry such as described in U.S. Pat. Nos. 5,560,363, 6,261,233 and 5,900,928. In the method according to the invention, the exercise is preferably continued until the mean blood flow or velocity in the artery radialis or subclavia increases with at least 10, 20, 40, 60, or 100%.

Alternatively, the reduction of the tension or the release of hypertension in the scalenius muscles may be determined by measuring an increase in the rotation angle of the Cervical Range of Motion (CROM). Methods for determining the CROM are described in Youdas et al. (1991, *Phys. Ther.* 71:98–106), Viitanen et al. (1998, *Br. J. Rheumatol.* 37:377–381) and Wolfenberger et al. (2002, *J. Manipulative Physiol. Ther.* 25:154–160). The rotation angle of the CROM as defined by the muscular resistance is preferably determined, as opposed to the rotation angle of the CROM as defined by the arthrogenic resistance (see FIG. 25). An increase in the rotation angle of the CROM is therefore a direct measure of the reduction of the tension or the release of hypertension in the scalenius muscles. In the method according to the invention, the exercise is preferably continued until the rotation angle of the CROM increases with at least 10, 15, 18, 20, or 25 degrees.

Usually the reduction of the tension or the release of hypertension in the scalenius muscles as determined by the above described increase in blood flow velocity or increase in rotation angle of the CROM are already achieved when the exercise is continued for at least 1 minute. In a preferred method according to the invention, the exercise is therefore continued for at least 1, 2, 3 or 4 minutes.

In the method according to the invention the training regime preferably comprises performing the exercise at least 1, 2, 3 or 4 times per day. Performing the exercise 4 times per day is usually sufficient to enlarge the costoclavicular space and to compensate the negative effects of hypertension of the scalenius muscles. Performing the exercise for longer times than indicated above or more frequent usually produces a better effect in reduction of the hypertension through training.

In the method of the invention, the object to be manipulated by the subject and held by pinch-grip force of the subject's fingers may be a writing instrument, a mouse or similar device, a stroke-making element for use in sport, such a tennis, squash, badminton or racquetball racket, a baseball bat or a golf club, an element for playing a musical instrument, such as a plectrum, a bow or a drum stick, or a tool such as a screw driver. In general, the object may be a device for monitoring a muscle or group of muscles as essentially herein described below. Preferably the object or device is a writing instrument as described herein below. The writing instrument may e.g. be a ballpoint pen or similar instrument. A particularly preferred writing instrument is a NoRSI™ sensorpen as available from Tensor B. V. (Breda, The Netherlands; see also www.norsiweb.com). The NoRSI™ sensorpen generates a different light signals for each of the first, second and third threshold values defined above, respectively a single flash, a flash repeated at low frequency and a flash repeated at high frequency. An equivalent of the NoRSI™ sensorpen that generates at least one signal, which is not necessarily a light signal but may also be a sound or other signal, when at least one of the first, second or third threshold value is exceeded, are equally applicable in the method of the invention. Included in the equivalents of the sensorpen are equivalents of which at least one of the first, second or third threshold value may be adjusted to or is set at a value that does not differ by more than 75, 50, 25 or 10% from the corresponding average value as set in the NoRSI™ sensorpen.

A further preferred writing instrument is an instrument that comprises a sensor that generates a fourth signal when a fourth threshold value is exceeded. The sensor generating the fourth signal may be a sensor that generates a signal when the pressure exerted on the writing surface exceeds a fourth threshold value. Preferably, the fourth threshold value is at least 40, 60, 80, 100, or 150 grams, of which a value in the range of 60–70 grams is most preferred. Children tend to exert more force on the writing instrument compared to adults. The threshold value may therefore be set to a higher value for children, e.g. 80–100 grams.

In such instances where the object is a writing instrument, the exercise preferably comprises writing or comprises a writing exercise.

The method according to the invention preferably is a method for treatment and prevention of a disorder associated with hypertension of the scalenius muscles, whereby the disorder is selected from the group of disorders consisting of repetitive strain injury, acute and chronic post-whiplash syndromes, arthrose and pre-arthrose, discopathy, i.e. pressure on the intervertebral discs in the neck, including narrowing of the discs or herniated discs coinciding with pressure on the nerve roots and associated motor control deficiencies and sensory disorders, reflex dystrophy in the upper extremities and other vegetative disorders (such e.g. dizziness and tinnitis) resulting from hypertension in the neck area, tendinitidis, venous obstruction or reduced venous blood flow, coordination disorders during writing, writingcramp in children, frozen shoulders and shoulders arthritis or capsulitis resulting from immobilization or trauma, headaches, and carpal tunnel syndromes resulting from venous obstruction or reduced venous blood flow. The method may further be used to improve blood flow through the artery subclavia in preparation of chest surgery, e.g. open-heart surgery.

In a further aspect the method may be used for the treatment of mental stress related problems as well as compulsive behavior as a result of addiction (e.g. alcohol, nicotine, drugs, or gambling). Both mental stress related problems and compulsive behavior can be diverted by providing a training regime that comprises manipulating an object while maintaining a pinch-grip force exerted by the fingers on the object below a given threshold value as described above.

In a preferred embodiment of the invention, the training regime is administered to the subject through a telecommunication interface such as a telephone, a radio or a television, or more preferably a computer connected to a computer network such as an internet, e.g. the world wide web, or an intranet. E.g. the subject may obtain a subscription to a training program that is provided to the subject through the telecommunication interface, such as a subscription to a homepage on the internet (see e.g. www.norsiweb.com). Preferably the training program is personalized for the subject and may involve monitoring the progress made with respect to reducing the tension in the scalenius muscles or with respect to the relieve of symptoms of the above mentioned disorders. Depending on the progress the training program may be adjusted. Preferably the training program is controlled by a computer program. The training program may administer writing exercises to the subject.

In another aspect of the present invention, methods for treating patients having or at risk of having hypertension of the scalenius muscles comprise providing the patient with a questionnaire to assess the extent of the hypertension or risk of hypertension, determining from answers to the questionnaire the condition of the patient, selecting a program of pinch-grip exercises for the patient based on the determined condition, and providing instructions to the patient for performing the selected pinch-grip exercises. Preferably, this method will be performed over a telecommunications interface, such as the world web wide or other internet system, an intranet system, or other telecommunication or video interfaces. Usually, the selected pinch-grip exercise will comprise manipulating an object with a pinch-grip signal generator which generates a signal when the pinch-grip applied by the patient exceeds a threshold value. Specific examples of such objects are described herein below. Usually, the pinch-grip exercise will comprise the patient performing particular manipulative patterns while counting or otherwise tracking the number of times the patient's grip exceeds the threshold value, typically based on the number of "signals" which occurs when the applied pinch-grip exceeds the threshold value. Optionally, the method may further comprise instructing the patient to monitor at least one condition parameter, such as Cervical Range of Motion (CROM), blood flow, exercise difficulty, loss of strength, perception of hindrance, restriction of movement, general well-being, and the like. The program may still further comprise a series of exercises to be performed successively over time, where the individual exercises to be performed vary in at least one of difficulty, complexity, and duration. Particular programs for performing such exercise protocols are presently commercially available on the www.norsiweb.com website, owned and operated by Tensor B.V., assignee of the present application, Use of this website to the public first became available on Oct. 12, 2001.

In further aspects the invention relates to methods for monitoring a muscle or group of muscles that may be used in the above described methods for treatment and prevention, as well as to devices that may be used in these methods.

Thus, in a further aspect provides a method for monitoring a muscle or group of muscles, comprising the steps of measuring the load on a muscle or group of muscles, comparing the load with a first threshold value and generating a warning when the measured load exceeds the first threshold value.

This enables the use of a feedback system whereby the attention of the user is drawn to a situation in which he or she is moving towards a determined position possibly resulting in muscular problems.

Such a method can be used both preventively and therapeutically. The method can also be used to enhance comfort.

It is also pointed out that the muscle or group of muscles of which the tension or displacement is measured does not have to be the same muscle or group of muscles in which the possible symptoms occur; it is quite well possible for tension or displacement in a first muscle to be caused by another muscle or by general tensions not directly related to muscles.

The invention further relates to a device for monitoring a muscle or group of muscles, comprising sensor for measuring the load on the muscle or group of muscles, comparing means connected to the sensor for comparing the measured load with the determined first threshold value and signaling means connected to the comparing means for generating a warning signal when the measured value exceeds a threshold value.

It is the intention that such a device be used in performing the method according to the invention.

According to a first preferred embodiment the method comprises the measure that the time is measured from the moment the threshold value is exceeded, and a second warning signal is generated when the measured time exceeds a threshold value.

The invention also provides a device which is characterized in that the device comprises time measuring means connected to the sensor and the comparing means for measuring the time from the moment the threshold value is exceeded, and that the signaling means are adapted to generate a second warning signal when the measured time exceeds a threshold value.

A system is hereby obtained wherein a warning signal is only generated when a position which might lead to muscle problems is held for a determined time.

This prevents excessive use of warning signals, for instance when changing position and the like.

According to another preferred embodiment a part of the body connected to the muscle or group of muscles for monitoring is monitored and a warning signal is generated when the monitored part of the body performs a movement.

An additional signal is hereby obtained, for instance when a determined part of the body is caused to move repeatedly.

The sensor is preferably formed by a movement sensor or pressure sensor which is placed outside the body, but which is intended for mechanical connection to the body.

Medical intervention is hereby avoided, while a good coupling between body and sensor is still obtained.

So as to enhance the comfort of the device, the sensor is fitted with a wireless signal transmission path between the sensor and the signaling means.

BRIEF DESCRIPTION OF THE DRAWINGS

FIG. 1 is a schematic perspective view of a workplace with a computer which is provided with a device according to the invention, FIG. 2 is a perspective cross-sectional view of a ballpoint provided with sensors according to the invention, FIG. 3 is a schematic perspective view of a part of the human body, FIGS. 12 and 13 show two embodiments of the device according to the invention which are received in a writing instrument.

FIGS. 28A and 28B illustrate a questionnaire to gather patient information and personal data for use in the method of FIG. 27.

FIGS. 29 through 38 illustrate particular exercise protocols accessible over the internet or world wide web in the methods of FIG. 27.

FIG. 39 illustrates a questionnaire for recording performance and results after a particular exercise protocol is performed according to the method of FIG. 27.

DETAILED DESCRIPTION OF THE INVENTION

Figure 4A:
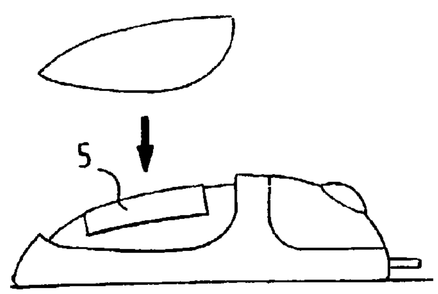
FIGS. 4, 5 and 6 show perspective views of computer mice into which the device according to the invention is integrated.

A device 1 for preventing RSI by avoiding overload of muscles comprises means 2 for measuring a load on the muscles, means 3 connected to load measuring means 2 for comparing the measured load with a determined first threshold value, and means 4 connected to comparing means 3 for generating a warning signal when the measured load exceeds the first threshold value. The function of signal generating means 4 does not otherwise have to be limited to generating a warning signal in the case of too high a muscle load, but these means can also be adapted to generate a release signal when the muscle load once again drops below the threshold value.

Load measuring means 2 can herein directly measure the load exerted by the muscles, but it is also possible for these measuring means to measure the load indirectly by detecting a movement of a part of the body resulting from the load on the relevant muscles.

In the first case the load measuring means 2 can comprise one or more sensors which are connected to a tool 6 which is operated by the muscles. As sensor 5 can be used for instance a pressure sensor with which a pressure force or grasping force of the muscles can be measured. The use of a strain sensor to measure a tensile force can however also be envisaged.

Figure 4B:
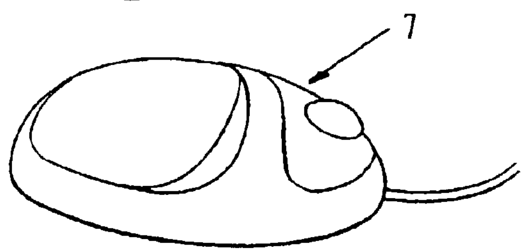
Figure 5A:
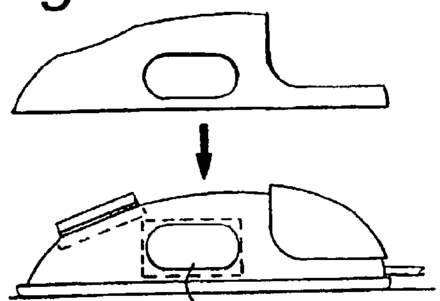
Figure 5B:
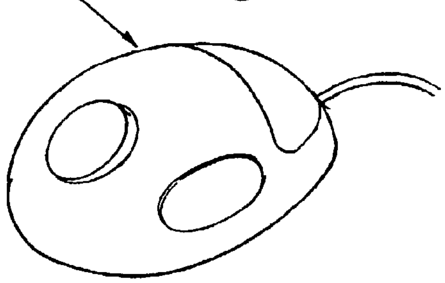
Figure 6A:
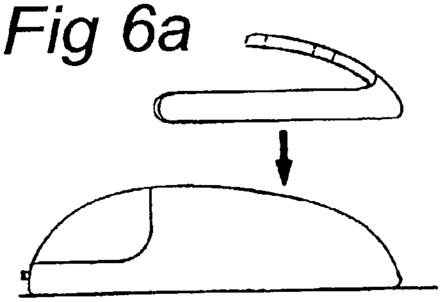
Figure 6B:
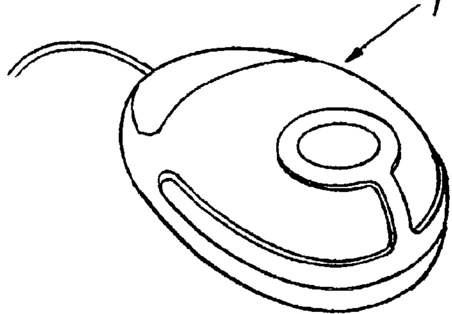
Figure 7:
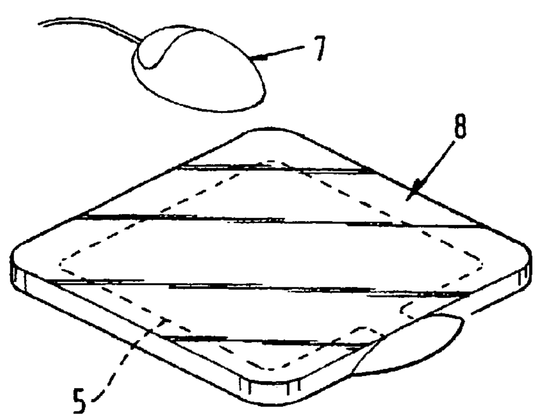
FIG. 7 is a perspective view of a mouse mat with the device therein.
Figure 8:
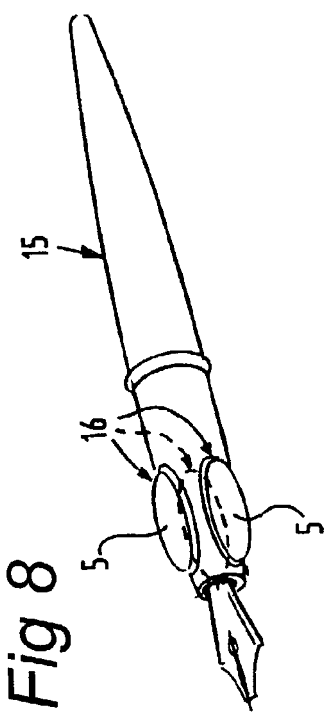
FIG. 8 shows the application of a device for preventing RSI according to the invention in a writing instrument.

Sensor 5 can be arranged in a computer 7 (FIG. 4, 5 and 6) or in a mouse mat 8 (FIG. 8.).

Figure 21:
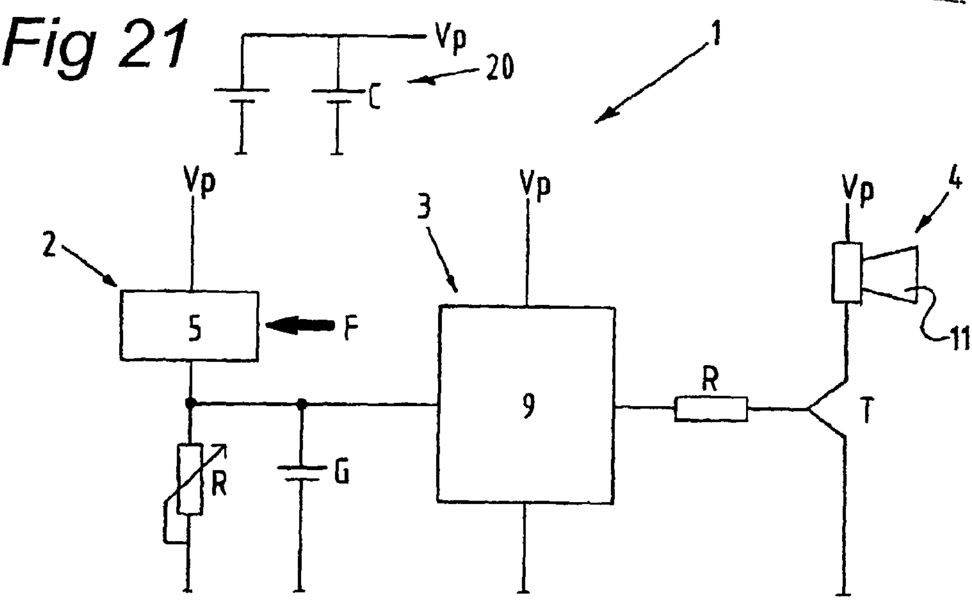
FIG. 21 shows a simplified circuit diagram of the device according to the invention.

As stated, sensor 5 is connected to comparing means 3, which can for instance take the form of a suitably programmed electronic circuit. This electronic circuit can be embodied as integrated circuit in the form of microchip 9 (FIG. 21). On this chip 9 can also be accommodated the signal generating means 4 which can likewise be formed by a programmed electronic circuit.

Sensor 5 and microchip 9 are herein connected to a power supply 20, for instance a battery.

The signal generating means 4 can further comprise a light source 10 and/or a sound source 11. Light source 10 can herein be a LED, which is relatively small and requires little energy.

Figure 22:
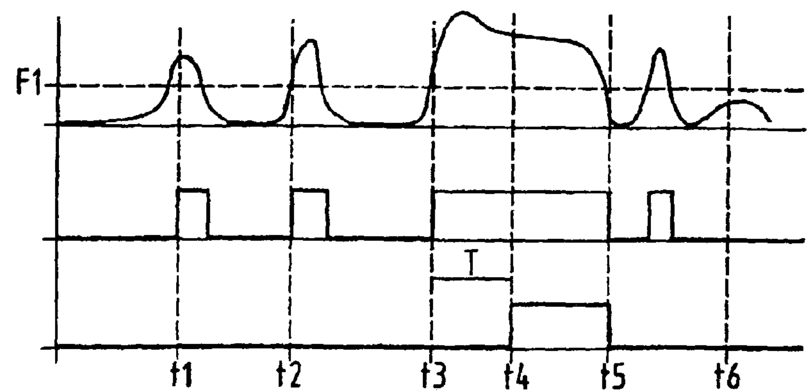
FIG. 22 is a diagram of the progression of the load in time and the operation of the device resulting therefrom.

The principle of the method according to the invention can be seen in FIG. 22. At points in time t1, t2 and t3 the sensor 5 is pressed in. As soon as the force exerted by the muscles on sensor 5 is greater than the threshold value F1, a clock is started internally in microchip 8. If the load falls below the threshold value again within a predetermined time T, nothing will happen, as can be seen at the points in time t1 and t2 . If the force exerted on sensor 5 remains greater than the threshold value F1 for longer than the time T, a warning signal will be generated after this time has elapsed for as long as threshold value F1 remains exceeded. For an optimal result the threshold value of the force F1 and the delay time T can be adjusted independently of each other.

When the load measuring means are accommodated in a mouse 7 or mouse mat 8, the rest of the device can also be accommodated therein, although it is also possible to include the comparing means 3 and signal generating means 4 in the form of an application program in a computer 12 connected to mouse 7. Computer 12 can therefore be programmed here to log the number of touches on a keyboard 14 connected to the computer, which may also form an indication of imminent RSI symptoms.

In the case computer 12 is used, the signals generated by signal generating means 4 can take form of an animation. A cartoon character 13 can for instance be shown herein, the facial expression or even the general state of which forms an indication for the presence or absence of muscle tensions which involve the risk of RSI.

Computer 12 can herein be programmed such that the facial expression or state of the FIG. 13 changes gradually as the measured muscle tension increases or decreases. The computer can further be programmed such that the FIG. 13 gives information on the basis of which the user can adjust the load on his muscles, for instance by changing working posture or by temporarily interrupting his activity.

In order to encourage users to adopt a good working posture and good working habits, computer 12 can be programmed to keep a score, which incorporates the frequency of (imminent) overload of the muscles. This score can be displayed on the relevant computer, wherein the user can then try to improve his score, while it is also possible to mutually connect a number of computers 12 in a network, which opens up the possibility of an "RSI-competition".

Figure 10:
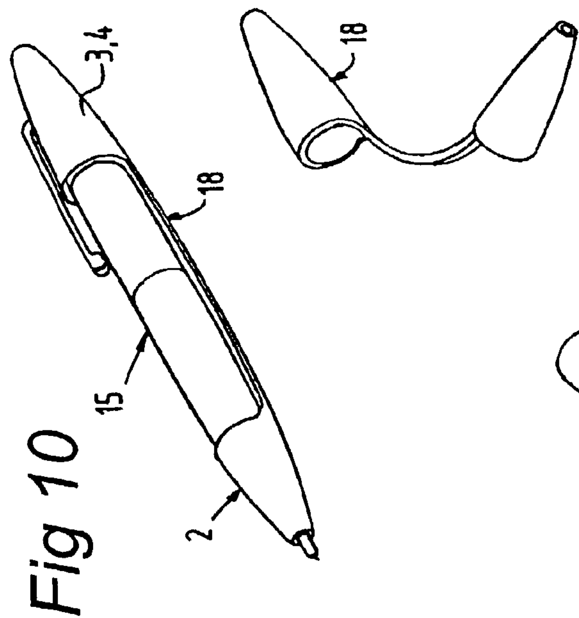
FIGS. 9, 10 and 11 show alternative embodiments of the device according to the invention arranged on a writing instrument.
Figure 11:
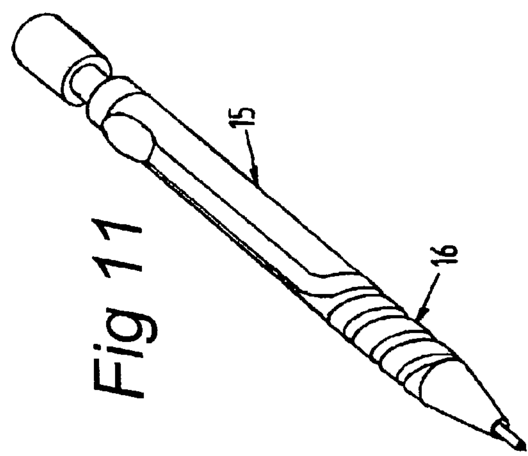
Figure 9:
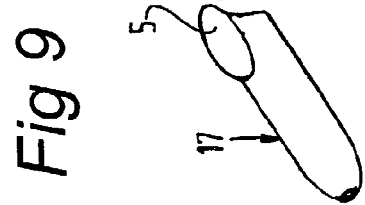

In addition to the computer mouse, writing instruments are also a source of RSI symptoms. In an alternative embodiment of the invention the sensors 5 are therefore mounted on a writing instrument 15 (FIG. 8). Each sensor can herein be integrated with a comparing circuit and signal generating circuit in very small form to form a warning unit 16. This warning unit 16 can also be releasably connected to writing instrument 15. In that case the unit for instance takes the form of a single sleeve 17 (FIG. 9) or dual sleeve 18 (FIG. 10) which can be pushed or clamped round writing instrument 15. In the case of the dual sleeve the comparing means 3 and signal generating means 4 are then accommodated in the rear compartment and load measuring means 2 in the front one. Warning unit 16 could also take a self-adhesive form and for instance be wrapped round the writing instrument.

The different components of device 1 could also be received in the body 19 of writing instrument 15. A par 21 of writing instrument 15 can herein be of conventional structure, while device 1 is accommodated in the remaining part 22 (FIG. 12,13).

In the ballpoint pen 40 shown in FIG. 2 a part of housing 41 is provided with a pressure sensor 5.

Pressure sensor 5 is connected via two wires 49 to a circuit 44. Circuit 44 is powered by batteries 47 and a LED 45 is connected to circuit 44.

The ballpoint pen 40 is further provided with an ink cartridge 42. Because the present embodiment of the invention prevents the use of a clicking mechanism, the ballpoint pen can be closed by a cap 43. Further arranged is a transparent element 46, in a recess of which the LED 45 is placed. The space for the batteries is closed off by a cover 48.

Figure 19:
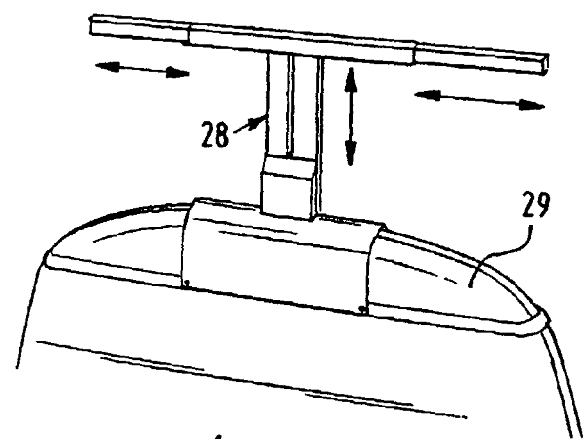
FIG. 19 shows an alternative embodiment of the device which is adapted to detect a movement of a body part connected to the relevant muscle, for instance the shoulder and which is connected to a piece of furniture.

Instead of a direct measurement of the load on the muscles, the movement of a part of the body connected to the muscles can, as stated, also be detected. It is possible for instance to choose the shoulder 23 for this purpose, which is pulled up when there is too great a strain on the arm muscles, wherein particular nerve paths 24 and/or blood vessels 25 are irritated or pinched by the first rib 26 and the collar bone 27 (FIG. 3). The movement of shoulder 23 can be detected by an adjustable bracket 28 which rests on the shoulder, is adjustable in height and width and which can be mounted on the back 29 of a seat (FIG. 19). A movement of the shoulder can herein result in a displacement of bracket 28, which can be detected by a movement sensor (not shown here). It is also possible to derive the movement of shoulder 23 from a force which is exerted by the shoulder on an article of clothing 30. For this purpose a pressure sensor 5 can be arranged in this article of clothing 30, for instance a bra.

The detected movement of the shoulder is again compared with a threshold value by comparing means and results in a warning signal being generated when this value is exceeded.

Figure 14:
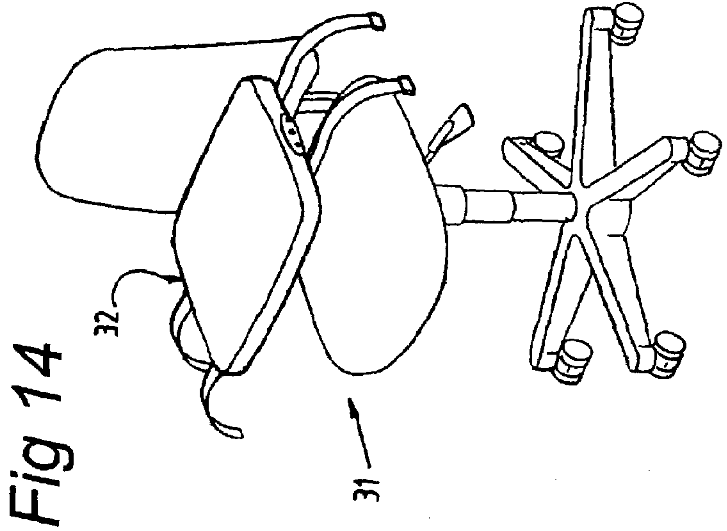
FIGS. 14, 15 and 16 show different options for devices according to the invention arranged in seat cushions.
Figure 15:
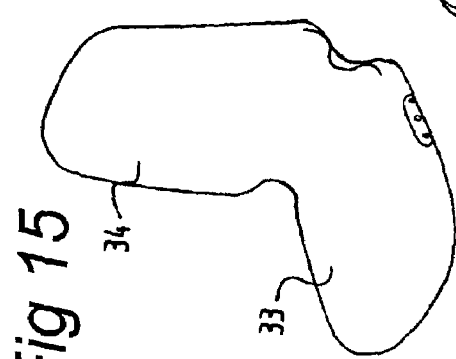
Figure 16:
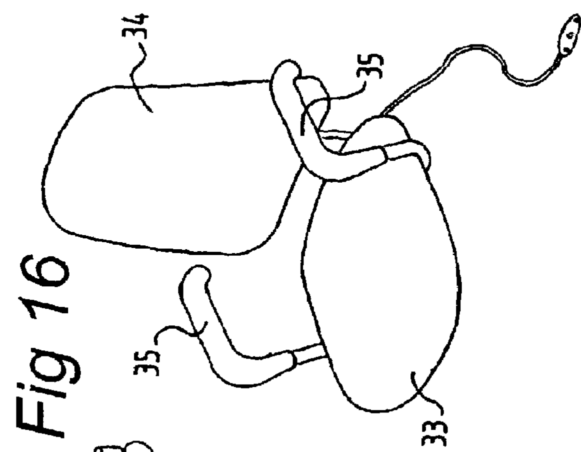
Figure 17:
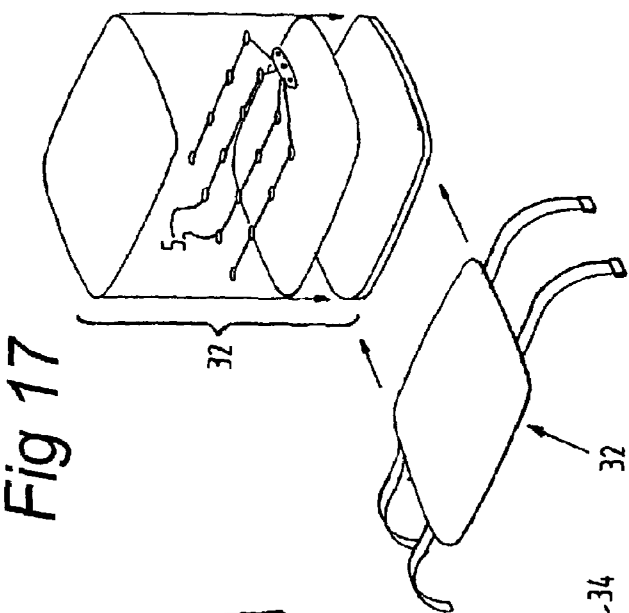
FIG. 17 shows the structure of a cushion having therein a device according to the invention.
Figure 18:
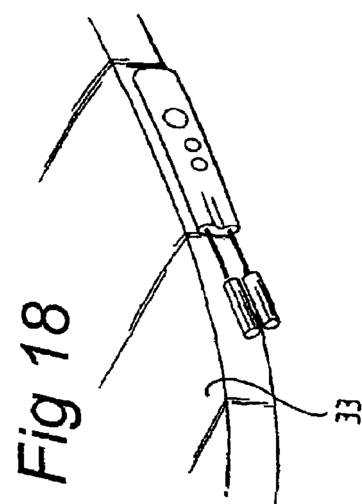
FIG. 18 shows a corresponding operating part of the device.
Figure 20:
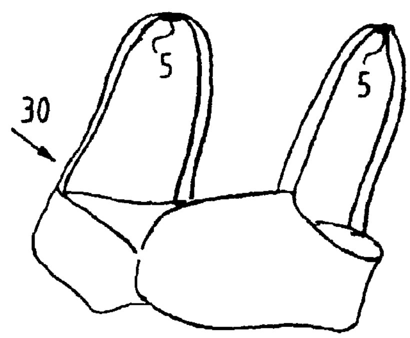
FIG. 20 shows a variant of the device for detecting the movement of the shoulder which is arranged in an article of clothing.

Instead of the movement of shoulder 23 the pressure exerted by the body of a user on different parts of a seat 31 could also be taken as a measure for the muscle tension and the risk of RSI. Pressure sensors 5 can be received for this purpose in a separate cushion 32 which is fixed on seat 31 (FIG. 14,17), or in the actual seatpart 33, seat back 34 and/or arm rests 35 of seat 31 itself (FIG. 15,16).

The invention thus makes it possible with relatively simple means to provide a warning when, as a result of for instance an incorrect working position or too great a number of repetitive actions, the danger of RSI is created, so that timely corrective measures can be taken.

Figure 27:
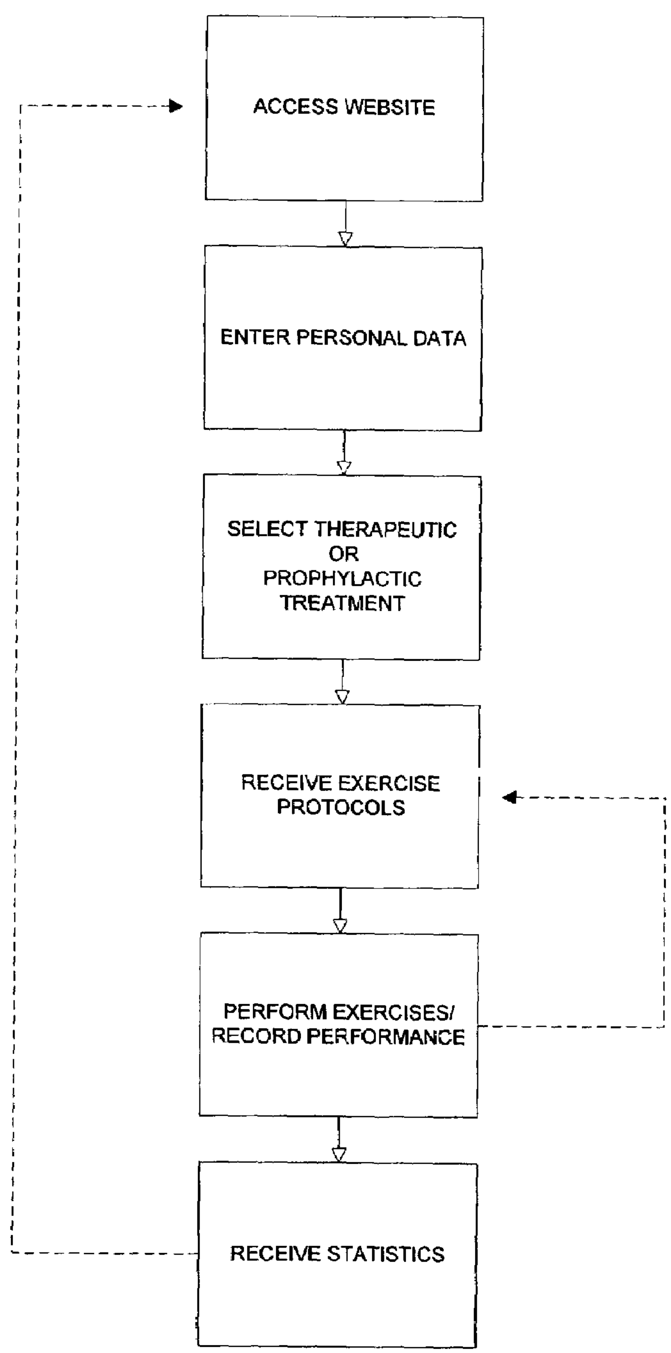
FIG. 27 shows a block diagram of a method for performing therapeutic or prophylactic therapy on a patient using exercise protocols according to the present invention accessed over a website.
Figure 29:
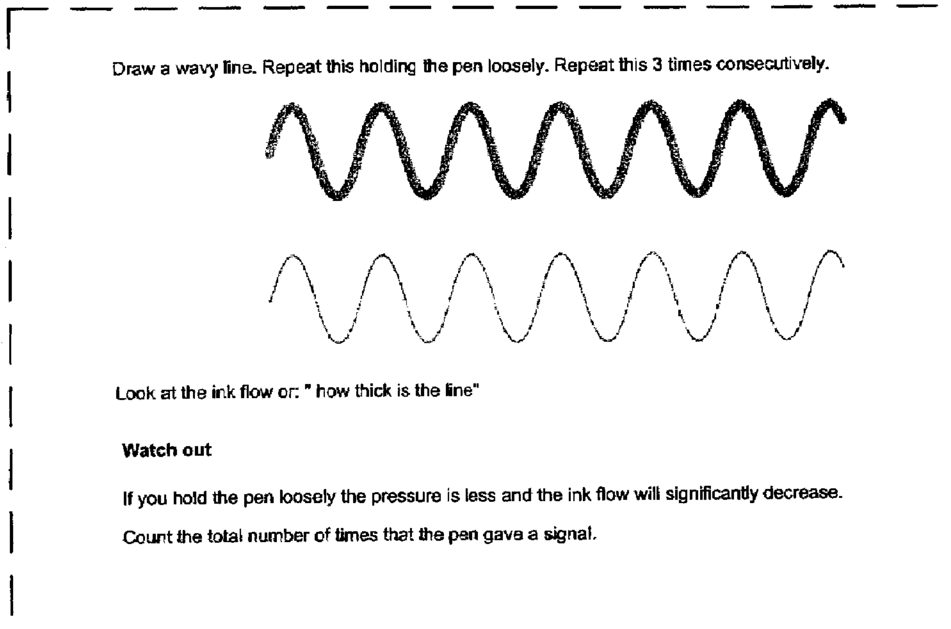
Figure 30:
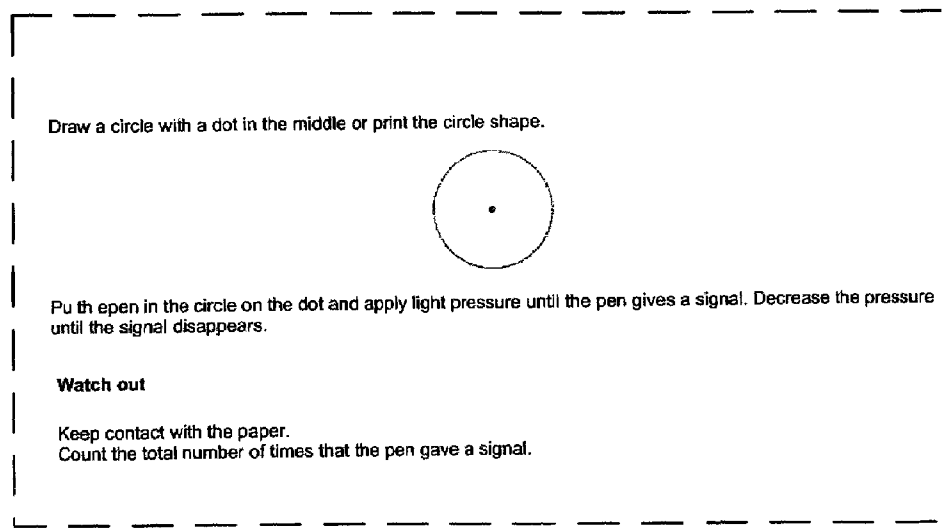
Figure 32:
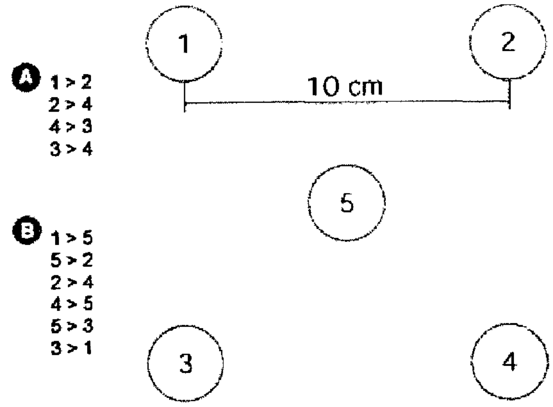

Referring now to FIG. 27, a method for performing a therapeutic or prophylactic therapy on a patient suffering from or at risk of hypertension of the scalenius muscles may be performed over a website. A presently available commercial website offering such methods is www.norsiweb.com, owned and operated by an assignee of the present patent application, which first became accessible to the public on Oct. 12, 2001, and is accessible on the filing date hereof. The methods described and claimed herein, however, are not meant to be limited to the operation of this particular website, and instead may be applied to other websites incorporating the described features as well as other forms of electronic communication, including video streaming, video conferencing, intranets, and the like. In order to facilitate the description, however, the following will be directed specifically at access of a website over the intranet or world wide web.

A patient first accesses the website in a conventional manner using a computer, workstation, or other intranet access device remote from the server which maintains the programming which runs the website. After the website has been accessed, the patient will be directed to a web page which will initially collect data on the patient and the patient's condition. An exemplary web page containing a questionnaire for obtaining patient data is shown in FIGS. 28A and 28B. This web page is taken directly from the commercial www.norsiweb.com website as it existed at the time of filing the present application. The information included on this web page is, of course, only exemplary of information which might be obtained and which could be used to determine exercises for a course of therapeutic or prophylactic treatment. Usually, this information need be obtained only once at the outset of a course of treatment, but optionally may be updated from time-to-time.

Once the patient data are collected, particular exercise protocols are provided to the patient over the internet, typically at the website but optionally via e-mail by other electronic communications. A number of exemplary exercise protocols are set forth in FIGS. 29–38, respectively. These exercise protocols are taken directly from the commercial www.norsiweb.com as it existed on the filing date of this application. It will be appreciated that these exercise protocols are only exemplary and are intended specifically for use with the exercise pen described in detail earlier in this patent application.

The exercise protocols may be performed singly or multiply in series, with individual protocols usually performed on successive days or alternatively with two or more different protocols performed on the same day. Periodically, and typically after each exercise protocol is completed, the patient will be asked to complete a result summary, such as that shown in FIG. 39 which is taken from the commercial www.norsiweb.com website as it existed on the filing date of the present application. The information gathered in this report allows program on the server (or optionally personnel with access to the server-maintained information) to keep track of the patient's progress, including preparing summary reports of such progress. The data also allow additional exercise protocol(s) to be selected for the patient in order to further achieve the desired therapeutic or prophylactic goal.

Although the invention is described and shown above on the basis of a number of embodiments, it is not limited thereto. Many variations are possible both in the embodiment and placing of the load measuring means and in the manner in which the measured quantities are processed and signaled. The scope of the invention is defined solely by the appended claims.

EXAMPLES

Example 1

Influence of a writing with a sensor pen on the blood flow velocity in the artery subclavia.

Blood flow velocity in the artery subclavia is proportional to its diameter, which is determined by the available space in the costoclavicular gate. Blood flow velocity in the artery subclavia is thus an indirect indication of the tension in the scalenius muscles, which determine the space in the costoclavicular gate.

Figure 23:
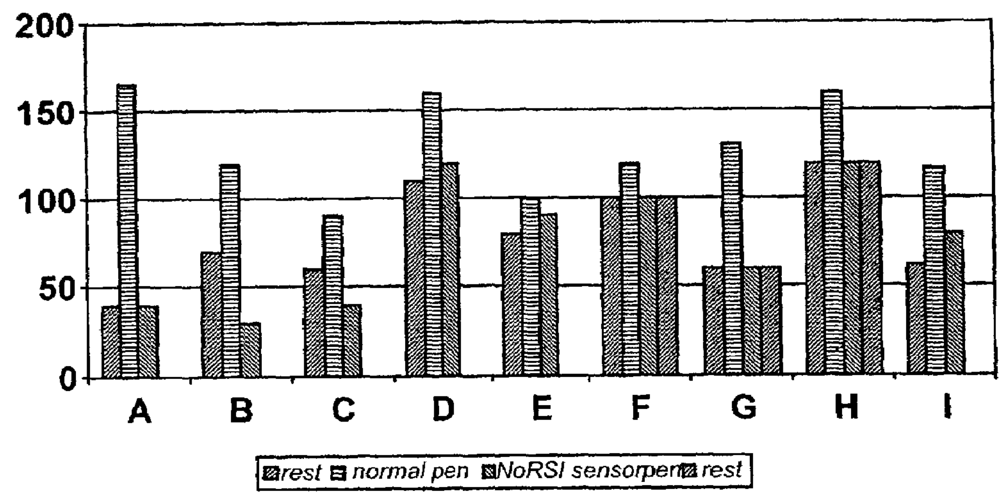
FIG. 23 shows a diagram of the blood flow velocities in the artery subclavia in 9 persons (A-I) while resting before writing, while writing with a regular ballpoint pen, while writing with a NoRSI sensor pen and for 3 persons (F-H) also while resting after writing.

Blood flow velocity in the artery subclavia was measured directly under the collarbone using ultrasound Doppler measurements. Blood flow velocities were measured in 9 persons (A-I) while resting before a writing exercise, while writing for 1 minute with a regular ballpoint pen, while writing for 1 minute with a NoRSI sensor pen, and in 3 persons (F-H) while resting after the writing exercise. Blood flow measurements are shown in FIG. 23.

Writing with a regular ballpoint pen caused significant narrowing of the costoclavicular gate in all 9 persons compared to the situation in rest. In contrast, a 1 minute writing exercise with the NoRSI sensor pen releases the tension in the scalenius muscles, thereby widening the costoclavicular gate and restoring the diameter of the artery subclavia to values close to or even wider than those while resting. Performing a writing exercise with the NoRSI sensor pen at least 4 times per day is sufficient to release hypertension in the scalenius muscles and widen the costoclavicular gate, thereby relieving the negative consequences of a narrowed costoclavicular gate.

The NoRSI sensor pen used in this exercise has a pinch-grip force pressure sensor set at a threshold value of 150–175 grams, and generates three different light signals for biofeedback control during the writing exercise. A first short light flash is generated when the threshold value is exceeded for a short time. A second low frequency flash signal (4 times) is generated when the threshold value is exceeded for more than 2.5 seconds. A third high frequency flashing signal is generated when the threshold value is exceeded for more than 10 seconds.

Example 2

Influence of writing with a sensor pen on the gain in rotation of the cervical range of motion.

Figure 24:
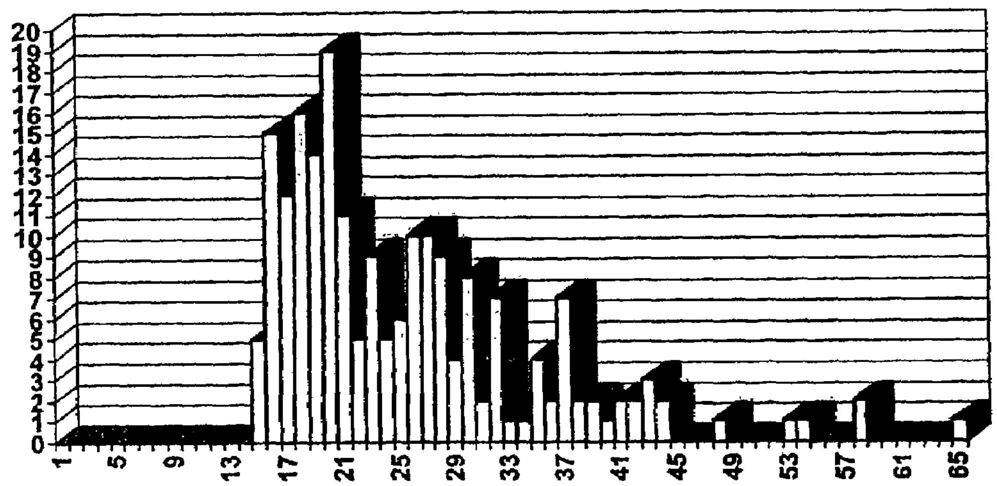
FIG. 24 shows a diagram of the gain in rotation of the Cervical Range of Motion (CROM) of 200 persons with neck, shoulder and/or arms complaints after a writing exercise with the NoRSI sensor pen. The X-axis shows the gain in rotation in degrees as measured before and after the writing exercise; the Y-axis shows the number of persons with a give gain in rotation.

200 persons with complaints in the neck, shoulder and/or arms (neck hernia, discopathy, arthrose/whiplash and/or frozen shoulder) were asked to perform a writing exercise with the NoRSI sensor pen as described in Example 1. The Cervical Range of Motion (CROM) was determined immediately before and after the writing exercise. The differences in rotation angle of the CROM in degrees before and after writing are shown in FIG. 24. Clearly persons with complaints in the neck, shoulder and/or arms gain at least 15 degrees in rotation angle of the CROM. The average gain in rotation angle of the CROM was 25,3 degrees in this population.

Figure 25:
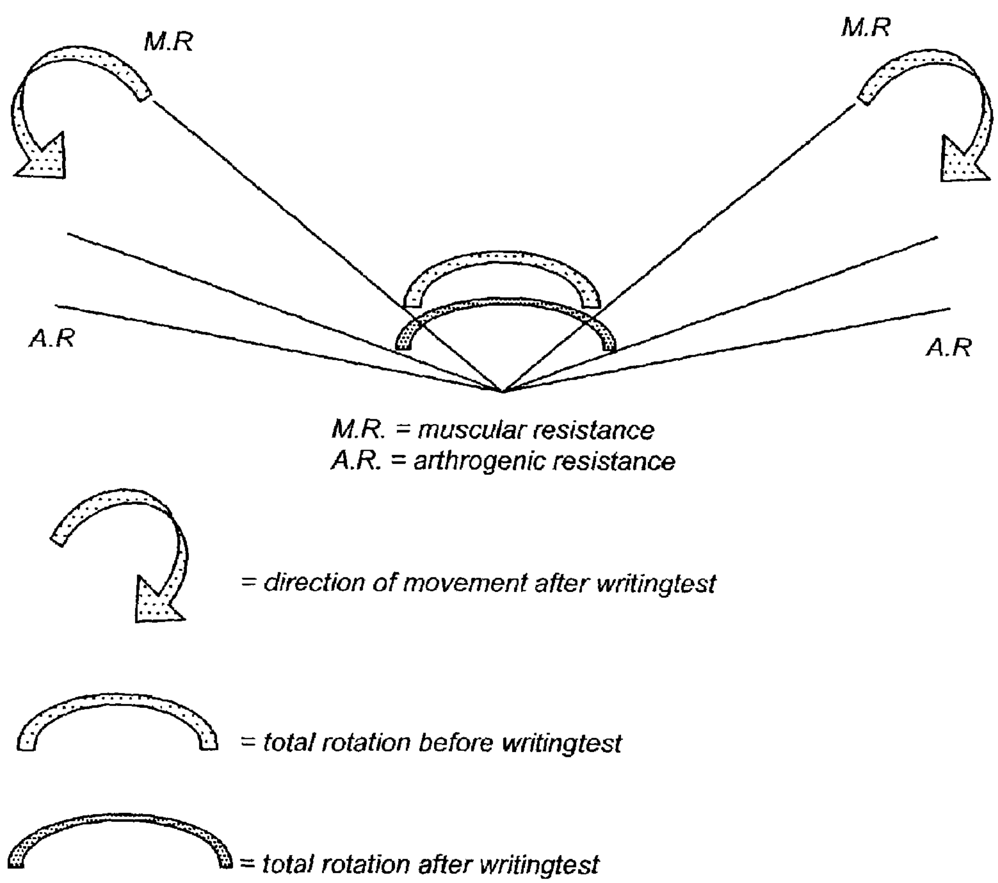
FIG. 25 shows a diagram of the Cervical Range of Motion as limited by the muscular resistance before and after a writing exercise and as limited by the arthrogenic resistance.
Figure 26:
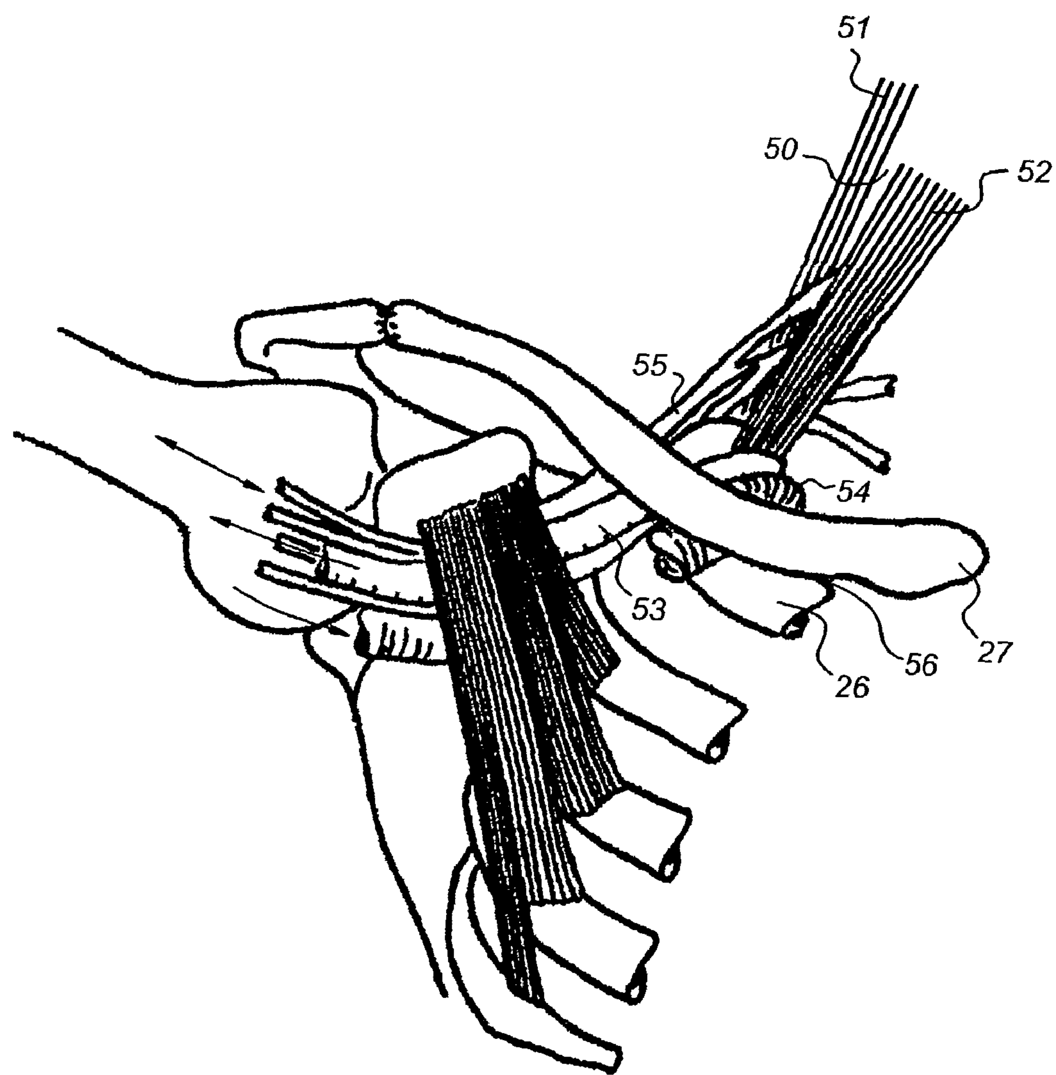
FIG. 26 shows the anatomy of the human neck-shoulder area.

In this experiment the limit of motion as a result of muscular resistance was measured, as opposed to the limit of motion as a result of arthrogenic resistance (see also FIG. 25). The gain in rotation of the CROM observed is therefore directly related to a release of tension in the scalenius muscles.

What is claimed is:

1. A method for treating a patient having or at risk of having hypertension of the scalenius muscles, said method comprising:

providing an object held by pinch-grip force by the patient, said object generating a signal when the pinch-grip force exceeds a first threshold value in range of 100 grams–250 grams; and providing instructions to the patient to manipulate the object with a pinch-grip force below the threshold value, wherein compliance is monitored based on the signal.

2. A method according to claim 1, wherein the threshold value is in range from 150 grams–175 grams.

3. A method according to claim 1, wherein the object generates a second signal when the time measured from the moment when the first threshold value is exceeded, exceeds a second threshold value.

4. A method according to claim 3, wherein the first threshold value is in the range from 150 grams–175 grams.

5. A method according to claim 4, wherein the second threshold value for the measured time is 2.5 seconds.

6. A method according to claim 3, wherein only the second signal is generated.

7. A method according to claim 3, wherein the first and second signals are generated by feeding to a collective signaling device on the object.

8. A method according to claim 1, wherein the patient has hypertension and an exercise is continued until the hypertension of the scalenius muscles is reduced or released.

9. A method according to claim 8, whereby the release or reduction of hypertension of the scalenius muscles is measured by an increase in blood flow velocity in the artery radialis or artery subclavia.

10. A method according to claim 9, whereby the blood flow velocity is measured by ultrasound or optical Doppler velocimetry.

11. A method according to claim 9, whereby an exercise is continued until the mean blood flow velocity in the artery radialis or artery subclavia is increased by at least 10%.

12. A method according to claim 8, whereby the release or reduction of hypertension of the scalenius muscles is measured by an increase in the rotation angle of the Cervical Range of Motion as determined by the muscular resistance.

13. A method according to claim 12, whereby an exercise is continued until the rotation angle of the Cervical Range of Motion is increased by at least 10 degrees.

14. A method according to claim 8, whereby an exercise is continued for at least 1 minute.

15. A method according to claim 1, whereby an training regime comprises performing an exercise at least once per day.

16. A method according to claim 1, whereby the object is a writing instrument, a mouse or similar computer input device, a stroke-making element for use in sport, an element for playing a musical instrument, or a tool.

17. A method according to claim 16, whereby the writing instrument is a sensorpen that generates at least one signal when at least one of a first, second or third threshold value is exceeded, whereby at least one of the first, second or third threshold value of the equivalent sensorpen is set or adjusted to a value that does not differ by more than 75% from the corresponding average value as set in the sensorpen.

18. A method according to claim 16 or 17, whereby the writing instrument is an instrument that comprises a sensor that generates a fourth signal when the pressure exerted on the writing surface exceeds a fourth threshold value.

19. A method according to claim 18, whereby the fourth threshold value is at least 60 grams–70 grams.

20. A method according to claim 16, whereby an exercise is a writing exercise.

21. A method according to claim 1, wherein the patient has hypertension and the hypertension results from a disorder is selected from the group of disorders consisting of repetitive strain injury, acute and chronic post-whiplash syndromes, arthrose and pre-arthrose, discopathy, including narrowing of the discs or herniated discs coinciding with pressure on the nerve roots and associated motor control deficiencies and sensory disorders, reflex dystrophy in the upper extremities and other vegetative disorders, including dizziness and tinnitis, resulting from hypertension in the neck area, tendinitidis, venous obstruction or reduced venous blood flow, coordination disorders during writing, writingcramp in children, frozen shoulders and shoulders arthritis or capsulitis resulting from immobilization or trauma, headaches, and carpal tunnel syndromes resulting from venous obstruction or reduced venous blood flow.

22. A method according to claim 1, whereby a training regime is administered to the subject through a telecommunication interface.

23. A method according to claim 22, whereby the telecommunication interface is a computer connected to a computer network.

* * * * *